United States Patent [19]

Coller

[11] Patent Number: 5,440,020

[45] Date of Patent: * Aug. 8, 1995

[54] PLATELET FUNCTION INHIBITING MONOCLONAL ANTIBODY FRAGMENT

[75] Inventor: Barry S. Coller, Dix Hills, N.Y.

[73] Assignee: The Research Foundation of State University of New York, Albany, N.Y.

[*] Notice: The portion of the term of this patent subsequent to Jul. 6, 2010 has been disclaimed.

[21] Appl. No.: 134,298

[22] Filed: Oct. 8, 1993

Related U.S. Application Data

[60] Division of Ser. No. 767,114, Sep. 27, 1991, which is a continuation-in-part of Ser. No. 474,293, Feb. 2, 1990, abandoned, which is a continuation of Ser. No. 851,711, Apr. 14, 1986, abandoned, which is a continuation-in-part of Ser. No. 745,415, Jun. 14, 1985, abandoned.

[51] Int. Cl.$^6$ .................. C07K 15/28; C12P 21/08
[52] U.S. Cl. .................. 530/388.7; 530/388.2
[58] Field of Search .................. 424/85.8, 130.1, 133.1, 424/141.1, 143.1; 435/70.21, 172.6, 240.27; 530/387.1, 38.1, 388.23, 388.7, 391.1, 388.2

[56] References Cited

U.S. PATENT DOCUMENTS 5,225,181  7/1993  Srivasta et al. .................. 424/1.1

OTHER PUBLICATIONS

Marchalonis et al. Antibody as a Tool John Wiley; pp. 224, 465 1982).
Vainchecker et al. Blod 59(3): 514–21 (1982).
Coller Blood 58 (Suppl.) p. 191(a) Abstract 674 (1981).
Thrlow et al. Br. J. Haematol 55(1): 123–34 (1983).
Pidard et al. J Biol Chem 258(2): 12581–6 (1983).
Coller et al. J Clin Invest. 72:325–338 (1983).
Jones et al. Br. J. Haematol 57: 621–631 (1984).
Coller J Clin Invest 76: 101–108 (1985).

*Primary Examiner*—David L. Lacey
*Assistant Examiner*—Phillip Gambel
*Attorney, Agent, or Firm*—Morgan & Finnegan

[57] ABSTRACT

There is provided a novel monoclonal antibody fragment which inhibits platelet function and may be useful in the treatment of thrombotic diseases. The fragment is produced by proteolytic digestion of the 7E3 monoclonal antibody.

3 Claims, 6 Drawing Sheets

FIG. 3A  DOG 3
(0.81 mg/ml)

FIG. 3B

FIG. 5

PLATELET FUNCTION INHIBITING MONOCLONAL ANTIBODY FRAGMENT

RELATED APPLICATIONS

This is a divisional of application Ser. No. 07/767,114 filed Sep. 27, 1991 which in turn is a continuation-in-part application of application Ser. No. 474,293, filed Feb. 2, 1990 now abandoned, which is in turn a continuation application of application Ser. No. 851,711, filed Apr. 14, 1986 now abandoned, which is a continuation-in-part of my application Ser. No. 745,415 filed 14th Jun. 1985, now abandoned.

BACKGROUND OF THE INVENTION

Blood platelets, also known as thrombocytes, function in the human body to provide for the coagulation of blood when the blood supply is exposed to potential loss, e.i., trauma, abrasions, and other hemorrhaging injuries. Platelets rapidly interact with damaged blood vessels and with each other to prevent the escape of blood cells and also facilitate the formation of a blood clot in which they become enmeshed so as to plug up any "leaks" in the vascular system. However, in certain disease states, such as thrombosis, it is desirable and even necessary, to inhibit blood platelet function. This is because the thrombus can either occlude the blood vessel and cause damage to the tissue being supplied with blood from that vessel (for example, myocardial infarction, stroke after vascular surgery, etc) or because the platelets and other thrombotic material can break off from the thrombus and lodge down-stream in blood vessels supplying other parts of the body (for example, venous thrombosis with pulmonary embolism, transient ischemic attacks, amaurosis fugax, strokes from the artificial hearts, etc).

Drugs currently utilized to counteract the platelet function suffer from a lack of potency and/or specificity. Thus, there is a continuing need for new and improved drugs that will inhibit platelet function in diseases characterized by thrombosis.

SUMMARY OF THE INVENTION

The present invention concerns a monoclonal antibody fragment which inhibits platelet function. The fragment was produced by the proteolytic digestion of the 7E3 monoclonal antibody, suitably with papain or pepsin. The 7E3 monoclonal antibody was produced in the following manner. Human blood platelets were injected into mice. The mouse spleen was removed and fused with a mouse myeloma by a modification of the technique of Levy et al. (Curr. Top. Microbiol. Immunol., 81, 164 (1978)). The fused cells were incubated and then further incubated in HAT medium (in which non-fused cells will not grow). The cells were then diluted out and screened in a screening assay for antifibrinogen receptor activity. There was selected one particular clone, designated 7E3 of the class $IgG_1$ which reacts with normal human blood platelets and with dog blood platelets, fails to react with thrombasthenia platelets or human platelets whose GPIIb/IIIA complex was disassociated with EDTA, reacts slowly with unactivated human platelets and more rapidly with ADP activated human platelets and completely blocks the interaction of fibrinogen with platelets induced by ADP.

BRIEF DESCRIPTION OF THE DRAWINGS

The FIGS. 1A and B, 2A and B and 3A and B respectively show as a) the plots of the change in platelet-rich plasma optical density after ADP addition to blood previously treated with the $F(ab')_2$ fragments at given previous intervals (FIGS. 1A, 2A, 3A)

b) a plot of molecules of $^{125}I$-7E3 bound per platelet ($\times 10^{-3}$) at certain time intervals after administration of the fragment (FIGS. 1B, 2B, 3B).

DESCRIPTION OF THE PREFERRED EMBODIMENTS a) Preparation

7E3 Monoclonal antibody was prepared according to the procedures set forth below:

Citrated platelet-rich plasma were prepared in accordance with the method of Coller et al., (Blood, 47, 841 (1976)), suspended in a suitable buffer and mixed with Freund's complete adjuvant. Injections of between about $1 \times 10^8$ to $5 \times 10^8$ washed platelets were made six times at weekly intervals into a BALB/c mouse intraperitoneally and a seventh similar injection without adjuvant at a similar time interval was given intravenously. Three days later the mouse was killed, the spleen removed, the cells separated and fused with a BALB/c mouse myeloma line in accordance with the method of Levy et al., (supra). In this method, the spleen cells and the myeloma cells in a ratio of 3.9:1 were pelleted together, the pellet suspended in polyethylene glycol (35%) in RPMI 1640 medium whereupon the cells were immediately centrifuged at low velocity. The solution was then diluted to about 25% of its previous concentration with RPMI 1640, the cells resuspended, recentrifuged and the supernatant removed. The supernatant was then incubated in a 5% $CO_2$ 95% air atmosphere in RPMI 1640 medium supplemented with fetal calf serum and thereafter selection made in the usual manner by adding HAT medium and aliquoting into microtiter wells. After two weeks, the supernatant of the wells that showed growth were screened for antifibrinogen receptor activity. The clones obtained by this method were selected for various qualities; one in particular, 7E3 was selected for certain qualities.

The antibody was isolated from the supernatant in the wells or flasks. Alternatively, the hybridomas were injected intraperitioneally into Pristane$^R$ pretreated BALB/c mice and the antibodies isolated from the ascitic fluid. The antibody was purified by precipitation with 50% saturated ammonium sulfate, resuspended in between 5 and 10% of the original volume in sodium phosphate buffer and dialyzed against the same buffer. Chromatography on protein A-SEPHAROSE CL-4B equilibrated with phosphate buffer was carried out, elution was with phosphate buffer followed by decreasing pH 0.1M citrate buffers. 7E3 antibody was eluted after the pH decreased to about 6.0. Protein elution was as monitored by ultra-violet spectroscopy at 280 nm.

Ouchterlony immune diffusion analysis against anti-$IgG_1$, $IgG_{2b}$, $IgG_3$, IgM and IgA sera indicated the exclusive presence of $IgG_1$.

Deposit with the A.T.C.C.: A deposit of cell line derivative, murine hybridoma 7E3, was made with the American Type Culture Collection, 12301 Parklawn Drive, Rockville, Md. on May 30, 1985. The accession number HB8832 was assigned after successful viability testing.

Purified antibody was then dialyzed overnight at reduced temperatures, suitably between about 0° C. and 10° C. preferably at 4° C. against a slightly acidic saline buffer of pH 3.5–6.5, suitably about pH 4.0, after which the freshly prepared pepsin was added in an amount equal to approximately 2% of the antibody's weight. The resulting solution was then incubated at about 37° C. for 12 to 24 hours. Digestion was stopped by dialyzing the solution against PBS, pH 7.4. Analysis by polyacrylamide gel electrophoresis indicated that the digestion was essentially complete.

Under somewhat different conditions, a Fab fragment can be prepared by digestion with papain, another proteolytic agent, namely, 0.1M acetate, 2 mM EDTA, 1 mM cysteine and including 1% w/w of papain for 6–8 hours at 37° C. at a pH of 4.5–6, suitably 5.5.

The resulting F(ab')$_2$ fragment of the 7E3 monoclonal antibody can then be further purified by chromatography on a material such as protein A SEPHAROSE CL-4B or DE-52 in order to be certain that any remaining traces of the whole 7E3 monoclonal antibody are removed.

EXAMPLE I

Antibody Production

A BALB/c mouse (Jackson Laboratories, Bar Harbor, Me.) was injected intraperitoneally with six weekly 0.2 ml injections of $3 \times 10^8$ washed platelets (citrated PRP washed twice in 0.15M NaCl, 10 mM Tris/Cl, 10 mM EDTA, pH 7.4 [TS-E]), resuspended in 1/10 to 1/20 of their original volume in TS-E, and mixed 1:1 with complete Freund's adjuvant. The seventh weekly injection was given intravenously into the tail vein and consisted of 0.3 ml containing $5 \times 10^8$ washed platelets resuspended in T-S without EDTA. Each of the seven platelet suspensions was obtained from a different donor. Three days after the last injection, the mouse was killed by cervical dislocation and the spleen removed. A suspension of spleen cells in RPMI 1640 was prepared by teasing the spleen apart. After erythrocytes were lysed with ammonium chloride, the spleen cells were fused with a nonsecretory BALB/c mouse myeloma cell line (X63-aG 8.653) that had been kept frozen in 10% DMSO, 90% fetal calf serum until one week before fusion, when it was thawed and maintained in the culture medium routinely used (RPMI 1640 supplemental with 10% fetal calf serum and 1,000 U of penicillin and 100 ug of streptomycin/ml). Fusion was carried out according to a modification of the method of Levy et al. (supra). Briefly, $2.7 \times 10^8$ spleen cells and $7 \times 10^7$ myeloma cells were pelleted together, the pellet was gently suspended in 2 ml of 35% polyethylene glycol in RPMI 1640 medium and the cells immediately centrifuged at 500 g at 22° C. for 6 minutes. The solution was then diluted with RPMI 1640 to 9% polyethylene glycol, the cells resuspended and immediately centrifuged at 230 g. for 6 minutes at 22° C. The supernatant fluid was then aspirated and the fused cells suspended in RPMI 1640 medium and supplemented with 20% fetal calf serum and 10% 109 medium (National Collection of Type Cultures). The cells were placed in a flask and incubated overnight at 37° C. in a 5% $CO_2$, 95% air atmosphere. The following day, the medium was made selective for successfully hybridized cells by adding hypoxanthine ($10^{-4}$M), aminopterin ($4 \times 10^{-7}$M), and thymidine ($1.6 \times 10^{-5}$M) after which the cells were aliquoted into 960 microtiter wells (Costar, Data Packaging, Cambridge, Ma.). Two weeks later, 574 wells showed growth and the supernatant fluids from 59 wells were positive in a screening assay for antifibrinogen receptor activity (see below). After an additional two weeks in culture, the positive clones were transferred to 24-well microtiter dishes (Costar) and fed with the same medium as above, but without the aminopterin. The clones were expanded and the cells that continued to produce antifibrinogen receptor antibody were suspended in 90% fetal calf serum-10% DMSO and frozen in liquid nitrogen.

The clones were subcloned by both limiting dilution technique and growth in soft agar to insure monoclonality.

Ascitic fluid rich in 7E3 antibody was prepared by intraperitoneal injection of Pristane-pretreated BALB/c mice with $5 \times 10^6$ hybrid cells that had been washed twice in 0.15M NaCl, 10 mM sodium phosphate, pH 7.4 (PBS).

Example II

Screening Assay 35 ul of PRP (platelet rich plasma) (adjusted to $3 \times 10^{11}$ platelets/liter) and 35 ul of the supernatant culture medium (or ascitic fluid) to be assayed were incubated together for 2–60 minutes in a well of a round-bottomed microtiter plate (Linbro Chemical Co., Hamden, Conn.). 5 ul of the fibrinogen-coated bead suspension was then added and the plate was mixed on a rotator (Tekator V, American Scientific Products, Edison, N.J.) for 5 minutes at 280 rpm. The wells were observed from the bottom with the aid of a magnifying mirror apparatus (Cooke Microtiter System, Dynatech Laboratories, Inc., Alexandria, Va.). Wells containing culture medium that had not been used for growing cells showed marked agglutination of the beads (rated as 4+), whereas the supernatant culture medium or mouse ascitic fluid from positive clones inhibited the agglutination, resulting in lower readings (0–3+).

EXAMPLE III

Antibody Purification

Culture supernatants were precipitated at 4° C. with 50% saturated ammonium sulfate and resuspended to between 1/20 and 1/10 of their original volume in 0.1M sodium phosphate buffer, pH 8.0. After dialysis against the same buffer, the samples were applied to a $0.8 \times 15.9$ cm column of protein A SEPHAROSE CL-4B that had been equilibrated with the phosphate buffer (after having been washed with both the phosphate buffer and a 0.1M citrate buffer, pH 3.0). The column was eluted with the phosphate buffer until the optical density of the eluate returned to base line, after which stepwise elution was accomplished with 0.1M citrate buffers of pH 6.0, 4.5, 3.5 and 3.0, as described by Ey, et al., (Immunochemistry, 15, 429 (1978)). 7E3 immunoglobins were eluted at pH 6.0. Protein elution was monitored by optical density at 280 nm and appropriate fractions were pooled and dialyzed against T-S containing 0.05% sodium azide. Antibody concentration was estimated by absorption at 280 nm, assuming $A^{1\%} = 15$.

EXAMPLE IV

Preparation of Fragment

7E3 Monoclonal antibody was prepared according to the procedures disclosed in the foregoing examples.

Purified antibody was then dialyzed overnight at approximately 4° C. against 0.2M sodium chloride, 0.2M acetate, pH 4.0, after which freshly prepared pepsin (1 mg/ml) was added in an amount equal to approximately 2% of the antibody's weight. The resulting solution was then incubated at about 37° C. for 12 to 24 hours. Digestion was stopped by dialyzing the solution against PBS, pH 7.4. Analysis by polyacrylamide gel electrophoresis indicates that the digestion was essentially complete.

The resulting F(ab')$_2$ fragment of the 7E3 monoclonal antibody can then be further purified by chromatography on a material such as protein A SEPHAROSE CL-4B or DE-52 in order to be certain that any remaining traces of the whole 7E3 monoclonal antibody are removed.

EXAMPLE V

Testing

The F(ab')$_2$ monoclonal antibody fragment was then tested for platelet function inhibition by the following method:

Three dogs were utilized. Dog No. 1 received a total of 0.17 mg/kg. in three injections given one hour apart. A blood sample drawn one hour after the last injection showed the following: 1) had a 61% decreased in the maximum extent of aggregation (Tmax) induced by 4 $\mu$M ADP; 2) having a platelet count of 220,000/ul (control$_{t=0}$=236,000); and 3) bound 45,400 molecules/platelets of $^{125}$I-7E3 (control=56,400), which suggests that 11,000 molecules of the F(ab')$_2$ fragment of the 7E3 monoclonal antibody are bound per platelet. Dog No. 2 received a single 0.57 mg/kg dose. 1.5 Hours later, the Tmax to ADP had decreased by 68% and the number of molecules of $^{125}$I-7E3 bound/platelet had decreased by 59% (from 62,5000 to 25,400); at 4 hours there was an 84% reduction in Tmax and a 64% reduction in molecules bound (22,500). The initial platelet count of 265,000 decreased to 253,000 at 1.5 hours and to 213,000 at 4 hours, but returned to 242,000 at 20 hours. Neither dog bled spontaneously.

Figure 1A:
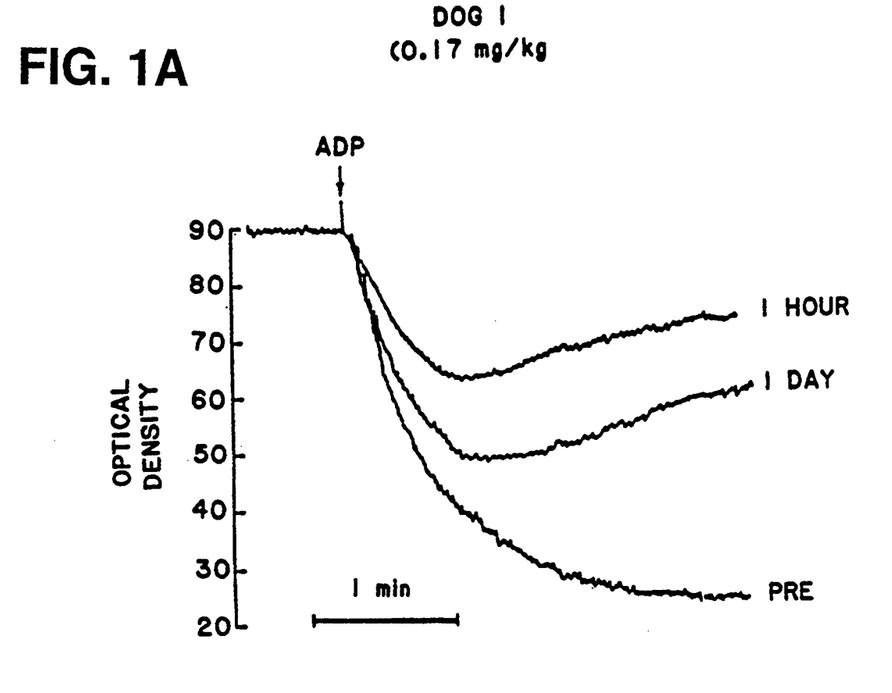
Figure 1B:
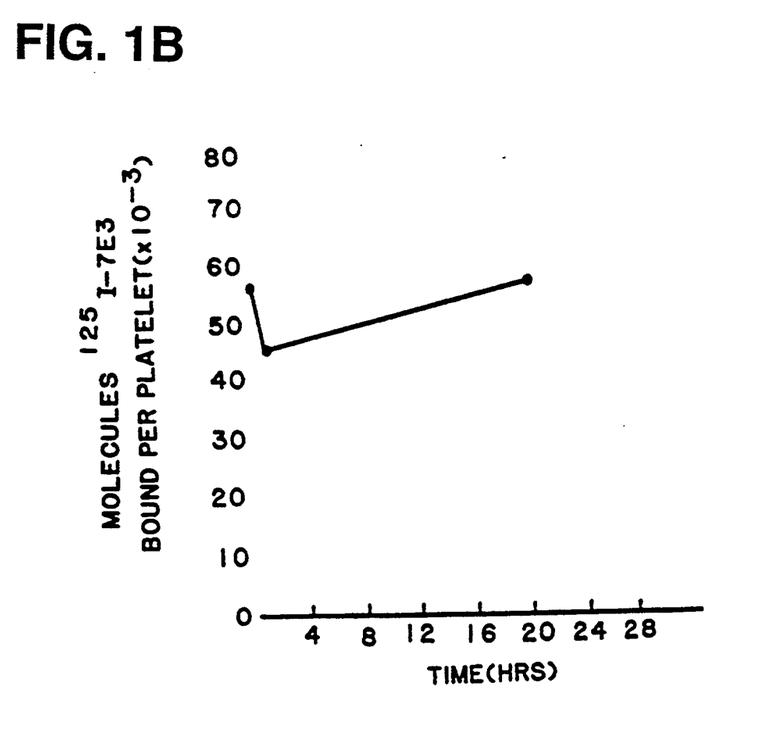
Figure 2A:
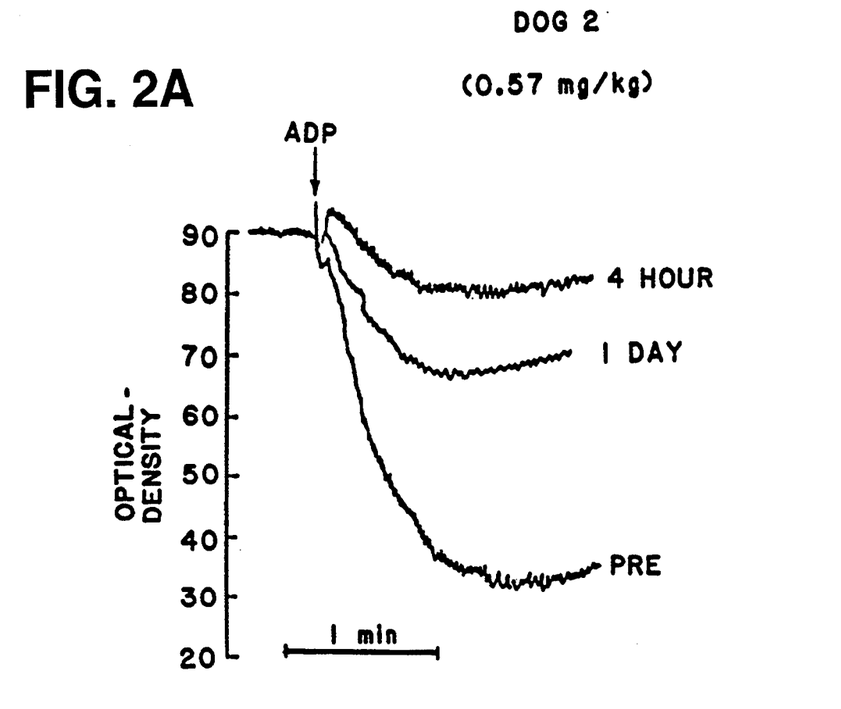
Figure 2B:
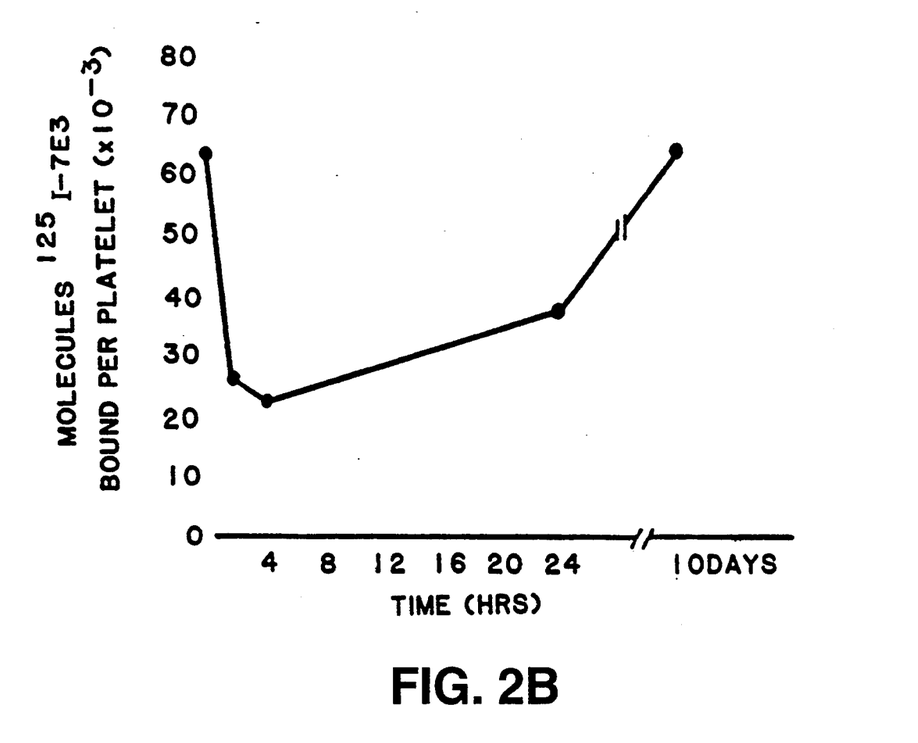
Figure 3A:
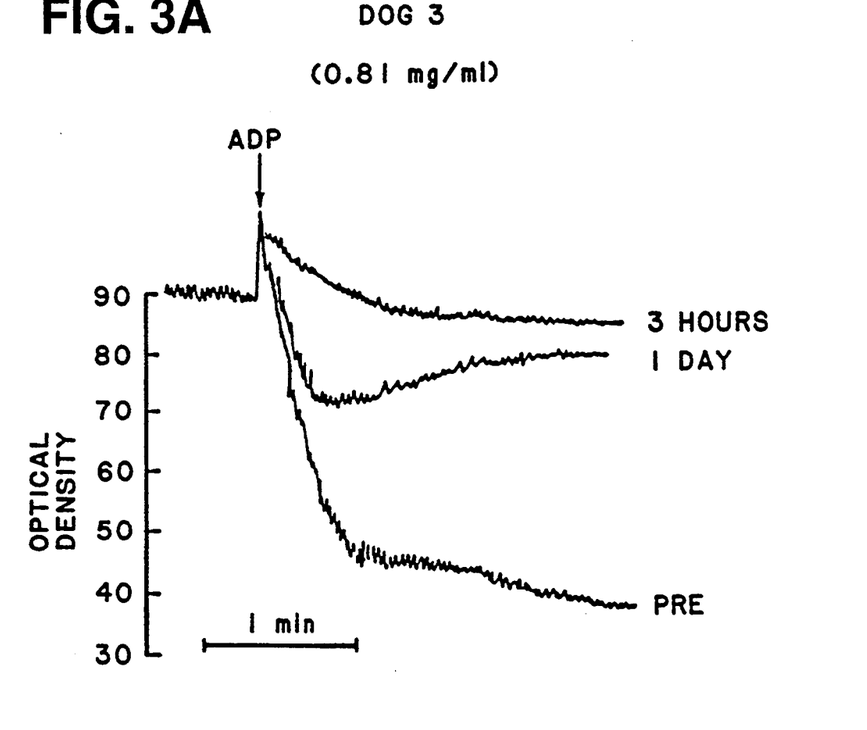
Figure 3B:
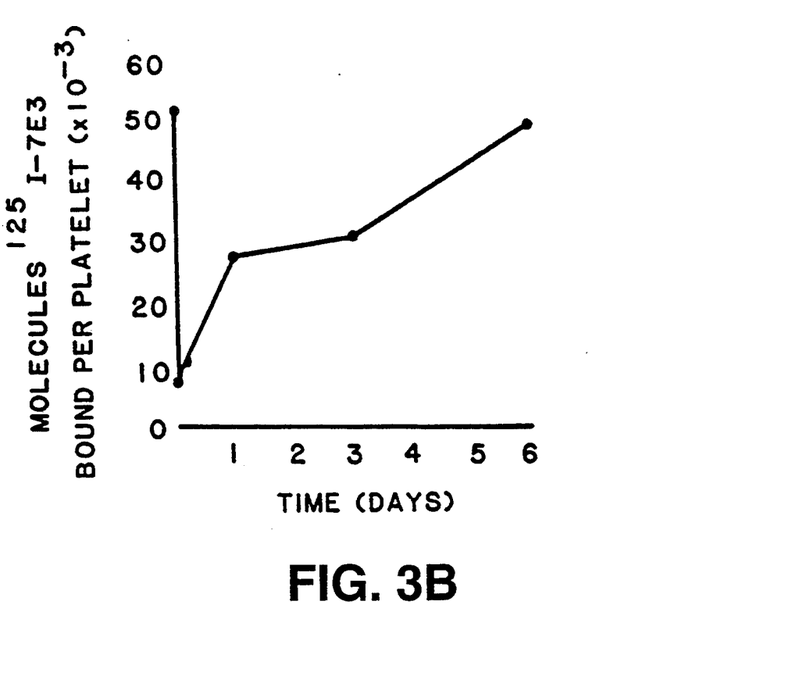
Figure 4A:
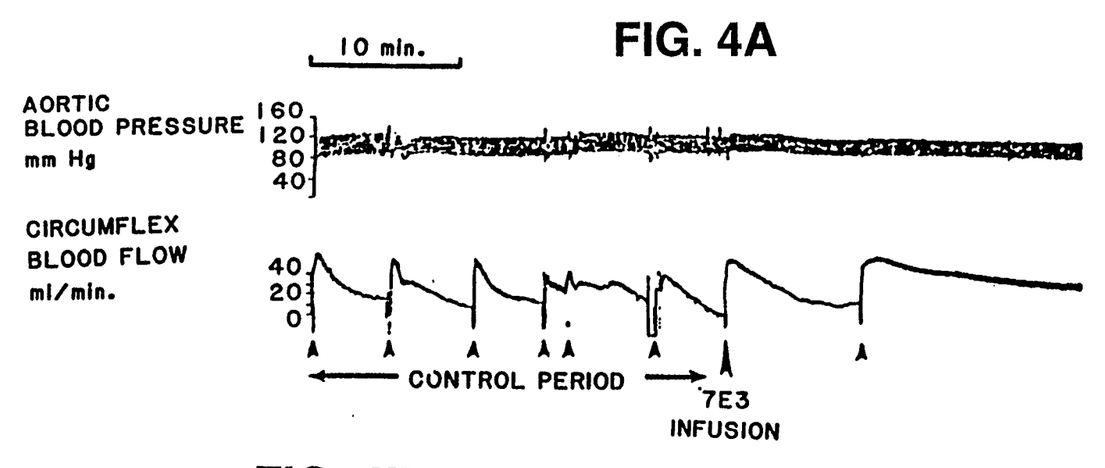
FIGS. 4A-D are a continuous set of plots for one test dog of aortic blood pressure and circumflex blood flow against time after administration of the $F(ab')_2$ fragments.
Figure 4B:
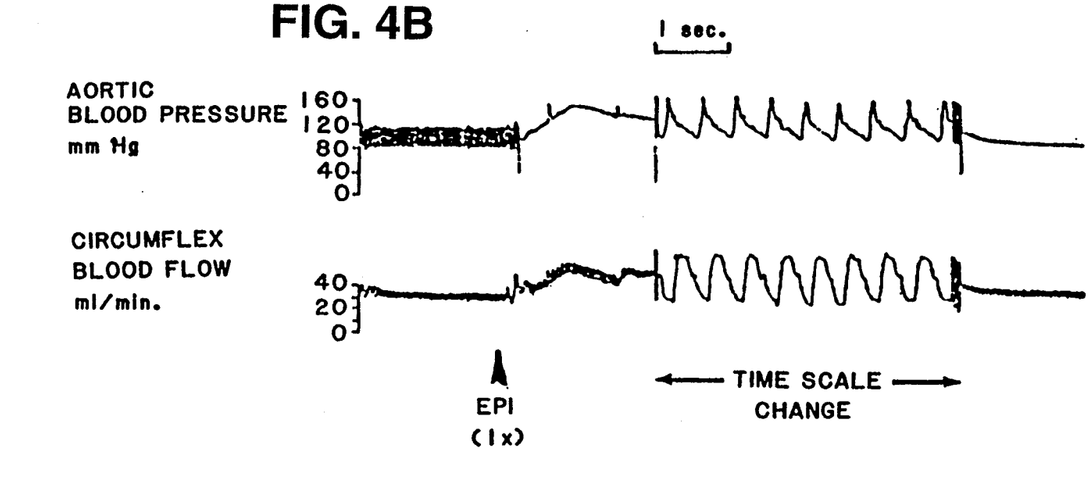
Figure 4C:
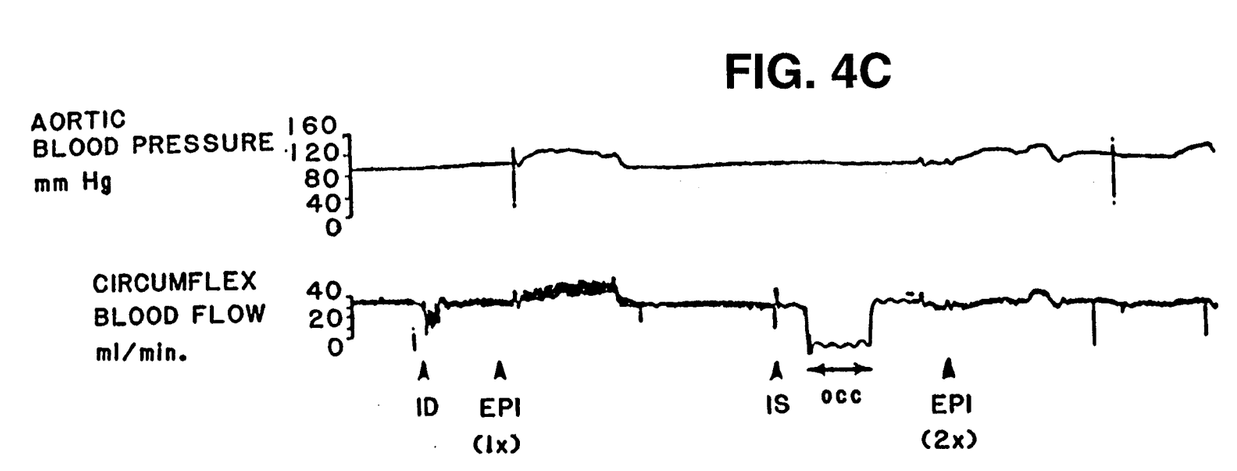
Figure 4D:
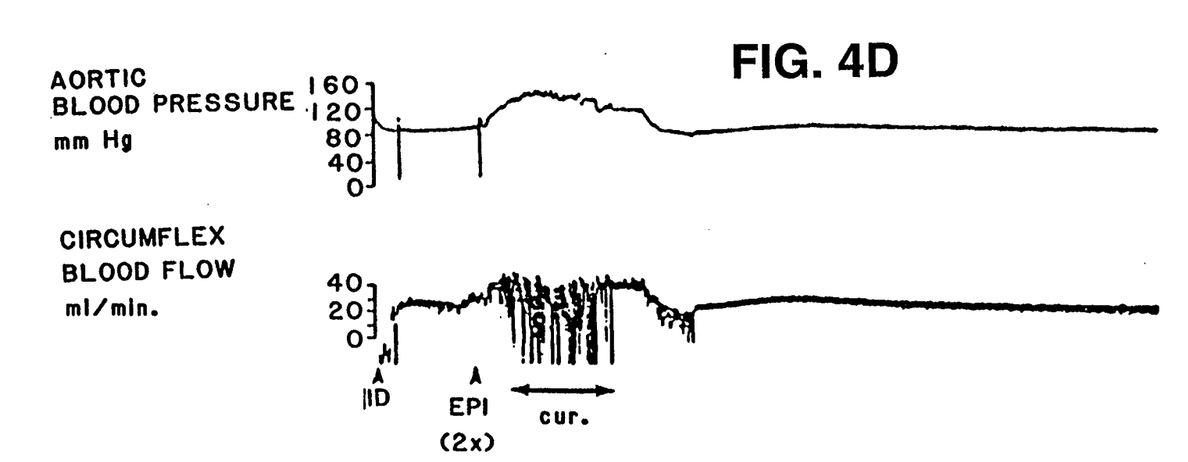

A third dog received 0.8 mg/kg of fragment as shown in FIG. 3A. These test results indicate that the F(ab')$_2$ fragment of the 7E3 monoclonal antibody can dramatically inhibit platelet function in vivo without causing profound thrombocytopenia.

EXAMPLE VI

In Vivo Testing

The cyclical blood flow reduction model has previously been described in detail (Folts, J. D., E. B. Crowell, Jr., and G. G. Rowe, 1976, Platelet Aggregation in Partially Obstructed Vessels and its Elimination with Aspirin, Circulation 54:365–370; Folts, J. D., 1982, Experimental Arterial Platelet Thrombosis, Platelet Inhibitors and their Possible Clinical Relevance, Cardiovasc. Rev. Rep., 3:370–382; Folts, J. D., Gallagher, K., and Rowe, G. G., 1982, Blood Flow Reductions in Stenosed Canine Coronary Arteries: Vasospasm or Platelet Aggregation?, Circulation 65:248–255), the disclosure of which is incorporated herein by reference. Briefly, either the circumflex coronary artery of an anesthetized dog or the carotid artery of an anesthetized monkey is dissected out and an electromagnetic probe is placed on it to measure blood flow. The artery is stenosed approximately 70% by placing a 3-4 mm long encircling plastic cylinder of the appropriate internal diameter around the outside of the artery. Cyclical reductions in blood flow due to platelet thrombus formation then commence whether spontaneously or after additional intimal damage is produced by brief (ca. 1 sec.) clamping of the artery with a hemostat. Within several minutes, blood flow in the vessel decreases to a critical level, after which the flow is abruptly restored to its original level, either by spontaneous embolization of the platelet thrombus, or by embolization induced by gently shaking the cylinder. Once established, the cyclical flow reductions persist if no intervention is made. The frequency and amplitude of the flow reductions can be temporarily enhanced by infusing 0.5 ug/kg/min. of epinephrine intravenously for 10 min.

The experimental protocol consisted of first obtaining samples of blood anticoagulated with either 0.01 volume 40% sodium citrate (for platelet aggregation and $^{125}$I-7E3 binding), or 0.037 volume 269 mM EDTA (for platelet counts), and then performing the surgery. After cyclical flow reductions were established, another set of blood samples was obtained and the antibody (0.7–0.8 mg/kg) was infused intravenously as a bolus. A final set of samples was obtained 30 min. after infusing the antibody. Platelet counts on the platelet-rich plasma were performed by microscopy after dilution and lysis of erythrocytes (Unopette, Becton-Dickinson), and whole blood platelet counts were performed by an electronic resistive particle counter (S+IV, Coulter Electronics, Hialeah, Fla.).

Results

Cyclical reductions in blood flow were obtained in 4 dogs and 4 monkeys. In all 4 dogs and 4 monkeys, infusion of the F(ab')$_2$ fragments resulted in complete cessation of the cyclical flow reductions and restoration of the control flow rate in 10 min. or less (FIGS. 4A–D). In the dogs, restoration of coronary flow correlated with the disappearance of ST segment deviations on the electrocardiograms, indicating the reversal of myocardial ischemia. The cyclical flow reductions could not be restored with epinephrine infusions of 0.5 or 1 ug/kg/min. for 10 minutes, increasing the intimal damage by repeated brief clamping of the vessel with a hemostat, passing current (1–2 mA) through the cylinder, or a combination of these provocations (FIGS. 4A–D). Postmortem histologic examination of the blood vessels confirmed the presence of extensive intimal damage.

Figure 5:
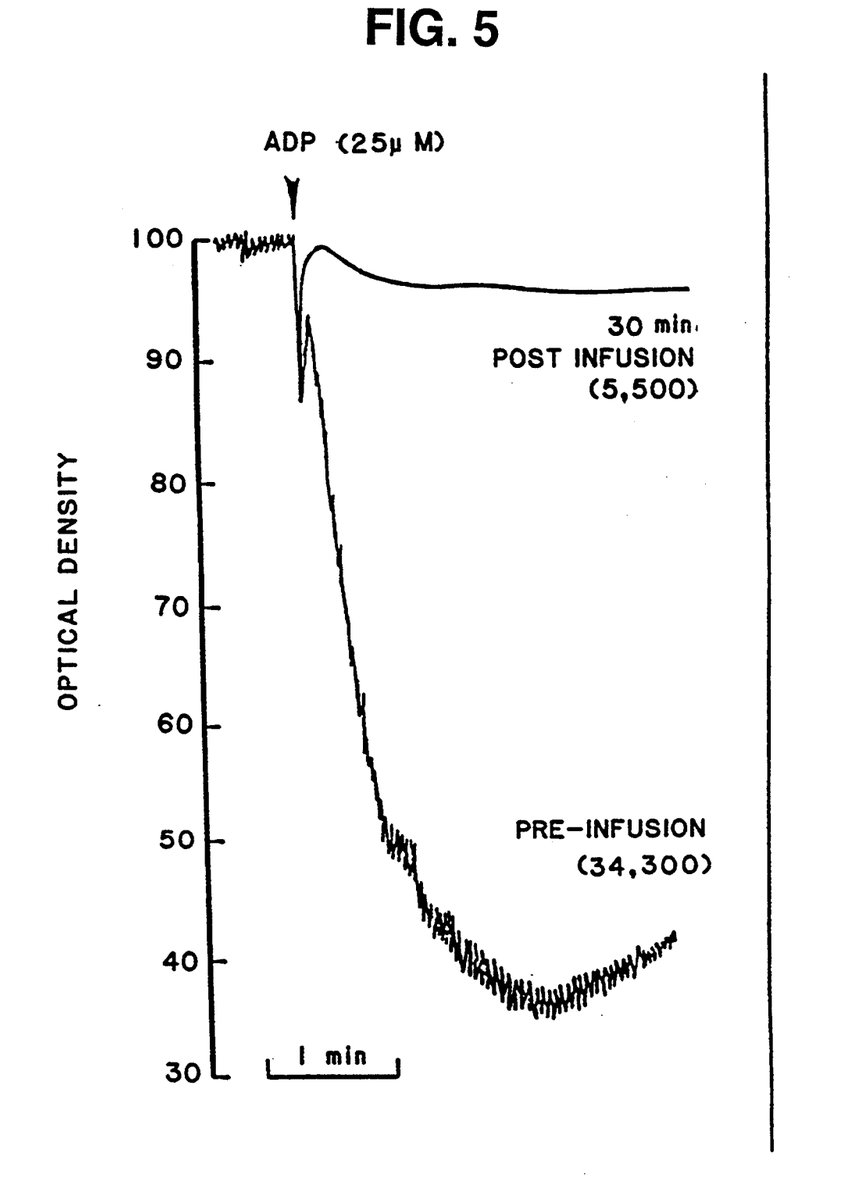
FIG. 5 is an optical density/time plot of ADP response pre and post $F(ab')_2$ infusion.

Platelet aggregation in response to ADP ($\leq$25 uM) was virtually abolished by the antibody infusion in all 8 animals, although the shape change response remained intact (FIG. 5). $^{125}$I-7E3 antibody binding studies were performed on 1 dog and 1 monkey. In both animals 84% of the GPIIb/IIIa receptors were blocked by the F(ab')$_2$ fragments (dog=34,300 molecules of $^{125}$I-7E3 bound per platelet before infusion and 5,500 after; monkey=49,700 before and 8,100 after). Platelet counts decrease by less than 15% in the 3 animals tested. None of the animals demonstrated a significant change in heart rate or blood pressure upon antibody infusion. There was no clear evidence of excessive hemorrhage from the operative sites after antibody infusion, although no objective data on blood loss were obtained.

EXAMPLE VII

Percutaneous transluminal coronary angioplasty (PTCA), whether by balloon or atherectomy, is an effective method of enlarging the lumen of stenosed coronary arteries. In this procedure, there is an inherent risk of acute coronary occlusion during and after angioplasty. The reported rate of coronary occlusion varies from 2% to 11% and is the major cause of in-hospital morbidity and mortality.

Acute coronary occlusion during and immediately after coronary angioplasty appears to be caused by the combination of deep arterial wall injury with resultant partially occlusive "intimal flaps" and superimposed thrombus formation.

Twenty-three patients scheduled for elective PTCA were treated with escalating doses of 7E3 F(ab')$_2$ fragments as follows: 0.15 mg/kg (4 patients), 0.20 mg/kg (6 patients), 0.25 mg/kg (4 patients), 0.30 mg/kg (5 patients), and 0.35 mg/kg (4 patients). The 7E3 F(ab')$_2$ fragment was prepared as a sterile, non-pyrogenic solution containing 2 mg of 7E3 F(ab')$_2$ per ml of 0.15M sodium chloride, 0.01M sodium phosphate, pH 7.2. The solution was screened for the presence of murine viruses, and stored at 2° C.–8° C. The 7E3 F(ab')$_2$ fragment was administered as a bolus 30 minutes prior to initiation of PTCA. For comparison, 5 control patients were also studied. Aspirin was withheld on the day of PTCA, but all patients received full doses of heparin, intracoronary and intravenous nitroglycerin during the PTCA procedure and diltiazem following PTCA.

Results

Median bleeding times were greater than 20 min. at 2 hrs. post infusion in all dose groups. Bleeding times remained >20 min. at 6 hrs. post infusion in the 0.25 mg/kg, 0.30 mg/kg and 0.35 mg/kg dose groups. In one patient in the 0.30 mg/kg dose group, bleeding of >20 min. was observed through 72 hrs. post infusion. In the control group, bleeding was prolonged to 18 min. at 2 hrs.; whereas, the normal bleeding time is about 7 min.

Inhibition of platelet aggregation in response to 20 $\mu$M ADP to $\leq$20% of baseline, was met at 2 hrs post infusion for the 0.30 mg/kg and 0.35 mg/kg dose groups. Aggregation of platelets increased to 25% of baseline at 6 hrs post infusion and returned to within 7% of baseline by 24 hrs post infusion for both dose groups.

Sheath removal occurred without difficulty or major bleeding in all dose groups within 24 hrs. One patient in the 0.30 mg/kg group underwent emergency bypass surgery. In this patient, platelet aggregation was inhibited at 2 hrs post infusion. The patient received 1 pack of platelets prior to surgery. Repeat platelet aggregation studies showed an improvement in platelet function. There was no undue intraoperative bleeding while on cardiopulmonary bypass. The patient was weaned off cardiopulmonary bypass, given an additional pack of platelets and surgery was completed in standard fashion. The remainder of the hospital stay was unremarkable.

Although twelve of the patients experienced adverse events which may be related to the use of 7E3 F(ab')$_2$, all patients recovered. This is in contrast to the 2% to 11% rate of coronary occlusion in PTCA without use of 7E3 F(ab')$_2$.

Human against murine antibodies (HAMA) responses were monitored pre-dose and post-infusion. Of the 23 patients treated, 12 patients exhibited low titer HAMA responses. The maximum anti-murine antibodies titer was 1:1600; the remaining titers were between 1:100 and 1:800.

Murine 7E3 F(ab')$_2$ fragment appears to be safe and effective when administered to PTCA patients at doses up to 0.35 mg/kg. The effect of 7E3 F(ab')$_2$ can also be reversed by infusion of platelets.

It will be apparent to those skilled in the art that many modifications, both of materials and methods, may be practiced without departing from the purpose and intent of this disclosure.

I claim:

1. An antigen binding fragment obtained by enzymatic digestion of a murine monoclonal antibody designated 7E3, produced by the ATCC HB 8832 hybridoma, which fragment:
   a. completely blocks the interaction of fibrinogen with platelets,
   b. prevents thrombus formation,
   c. readily reacts with both normal human platelets and dog platelets,
   d. fails to react with thrombasthemic human platelets or human platelets whose GPIIb/IIIa complex is dissociated with EDTA, and
   e. reacts more rapidly with ADP activated platelets.

2. The fragment of a murine monoclonal antibody of claim 1 wherein the enzymatic digestion is done by a proteolytic agent selected from the group consisting of papain and pepsin.

3. The fragment of a murine monoclonal antibody of claim 2 wherein the enzymatic digestion is done by a proteolytic agent consisting of pepsin.

* * * * *

UNITED STATES PATENT AND TRADEMARK OFFICE
CERTIFICATE OF CORRECTION

PATENT NO. : 5,440,020
DATED : August 8, 1995
INVENTOR(S) : Barry S. Coller

It is certified that error appears in the above-indentified patent and that said Letters Patent is hereby corrected as shown below:

Column 1, line 15:
   After the paragraph entitled "RELATED APPLICATIONS" insert as follows:

The present invention was supported by Grant #HL19278 from the National Institutes of Health. --

Signed and Sealed this

Fifth Day of December, 1995

*Attest:*

BRUCE LEHMAN

*Attesting Officer*     *Commissioner of Patents and Trademarks*